(12) United States Patent
Borzooeian et al.

(10) Patent No.: US 11,353,424 B2
(45) Date of Patent: Jun. 7, 2022

(54) LENGTH-BASED CARBON NANOTUBE LADDERS

(71) Applicants: Zahra Borzooeian, Brighton, MA (US); Mohammad E. Taslim, Needham, MA (US)

(72) Inventors: Zahra Borzooeian, Brighton, MA (US); Mohammad E. Taslim, Needham, MA (US)

(73) Assignee: Nano LC-12, LLC, Natick, MA (US)

( * ) Notice: Subject to any disclaimer, the term of this patent is extended or adjusted under 35 U.S.C. 154(b) by 108 days.

(21) Appl. No.: 16/660,446

(22) Filed: Oct. 22, 2019

(65) Prior Publication Data

US 2020/0200706 A1 Jun. 25, 2020

Related U.S. Application Data

(63) Continuation-in-part of application No. 16/383,552, filed on Apr. 12, 2019, now Pat. No. 11,079,387.
(Continued)

(51) Int. Cl.
*G01N 27/447* (2006.01)
*C12N 9/36* (2006.01)
(Continued)

(52) U.S. Cl.
CPC ..... *G01N 27/44726* (2013.01); *C01B 32/159* (2017.08); *C01B 32/172* (2017.08);
(Continued)

(58) Field of Classification Search
None
See application file for complete search history.

(56) References Cited

U.S. PATENT DOCUMENTS

| 4,555,490 | A | | 11/1985 | Merril | |
|---|---|---|---|---|---|
| 5,316,908 | A | * | 5/1994 | Carlson | C12Q 1/68 204/461 |

(Continued)

FOREIGN PATENT DOCUMENTS

WO 2008143281 A1 11/2008

OTHER PUBLICATIONS

Borzooeian, et al., "A high precision method for length-based separation of carbon nanotubes using bio-conjugagtion, SDS-PAGE and silver staining", PLOS One, 13(6): p. e0197972, Jun. 25, 2018.*
(Continued)

*Primary Examiner* — J. Christopher Ball
(74) *Attorney, Agent, or Firm* — Duquette Law Group, LLP

(57) ABSTRACT

Some embodiments provide methods and systems for creating ladder/standards as quality control tools for length-based separation of carbon nanotubes; determining the length purity; or measuring distribution of lengths of a collection of carbon nanotubes. Some embodiments further provide methods and systems for dispersing carbon nanotubes by conjugation of the carbon nanotubes with biomolecule moieties, specifically proteins. Further, some embodiments provide an indicator for length-based separation of carbon nanotubes via conjugation of one or more biomolecules onto the surfaces of the nanotubes. In some embodiments, such a method can include conjugating a biomolecule to the carbon nanotubes and subjecting the conjugated carbon nanotubes to silver-stained gel electrophoresis to separate the conjugated carbon nanotubes based on their lengths.

16 Claims, 17 Drawing Sheets

Related U.S. Application Data

(60) Provisional application No. 62/656,645, filed on Apr. 12, 2018.

(51) Int. Cl.
    *C01B 32/172*     (2017.01)
    *C01B 32/159*     (2017.01)
    *B82Y 35/00*     (2011.01)
    *B82Y 30/00*     (2011.01)

(52) U.S. Cl.
    CPC .... *C12N 9/2462* (2013.01); *C12Y 302/01017* (2013.01); *G01N 27/44756* (2013.01); *B82Y 30/00* (2013.01); *B82Y 35/00* (2013.01); *C01B 2202/02* (2013.01); *C01B 2202/34* (2013.01)

(56) References Cited

U.S. PATENT DOCUMENTS

| | | | |
|---|---|---|---|
| 5,449,758 A * | 9/1995 | Hartley | C07K 14/005 530/350 |
| 5,840,575 A | 11/1998 | Hyman | |
| 7,374,649 B2 | 5/2008 | Jagota et al. | |
| 10,060,910 B2 | 8/2018 | Coleman et al. | |
| 2004/0235016 A1 | 11/2004 | Hamers et al. | |
| 2006/0024808 A1 | 2/2006 | Darzins et al. | |
| 2006/0142148 A1 | 6/2006 | Ma et al. | |
| 2007/0258880 A1 | 11/2007 | Murakoshi | |
| 2008/0076816 A1 | 3/2008 | Bianco et al. | |
| 2010/0189626 A1 | 7/2010 | Tanaka et al. | |
| 2011/0108424 A1 | 5/2011 | Puget et al. | |
| 2012/0259098 A1 | 10/2012 | Baker, Jr. et al. | |
| 2012/0269721 A1 | 10/2012 | Weng et al. | |
| 2014/0262972 A1 | 9/2014 | Adiga et al. | |
| 2018/0148479 A1 | 5/2018 | Lim et al. | |
| 2018/0243692 A1 | 8/2018 | Borzooeian et al. | |
| 2019/0076075 A1 | 3/2019 | Miller et al. | |
| 2019/0317102 A1 | 10/2019 | Borzooeian et al. | |
| 2020/0031672 A1 | 1/2020 | Nihey | |
| 2020/0200706 A1 | 6/2020 | Borzooeian et al. | |

OTHER PUBLICATIONS

A. C. Dillon, Jones A, Bekkedahl T, Kiang C. Storage of hydrogen in single-walled carbon nanotubes. Nature. 1997;386:377-9.
Asuri P, Bale SS, Pangule RC, Shah DA, Kane RS, Dordick JS. Structure, function, and stability of enzymes covalently attached to single-walled carbon nanotubes. Langmuir. 2007 ;23 (24): 12318-21.
Bachtold A, Hadley P, Nakanishi T, Dekker C. Logic circuits with carbon nanotube transistors. Science. 2001;294 (5545):1317-20.
Bandow S, Rao A, Williams K, Thess A, Smalley R, Eklund P. Purification of single-wall carbon nanotubes by microfiltration. The Journal of Physical Chemistry B. 1997;101(44):8839-42.
Baughman RH, Zakhidov AA, de Heer WA. Carbon nanotubes—the route toward applications. science. 2002;297(5582):787-92.
Blum H, Beier H, Gross HJ. Improved silver staining of plant proteins, RNA and DNA in polyacrylamide gels. Electrophoresis. 1987;8(2):93-9.
Bonard JM, Stora T, Salvetat JP, Maier F, Stockli T, Duschl C, et al. Purification and size-selection of carbon nanotubes. Advanced Materials. 1997;9(10):827-31.
Borzooeian et al., "A high precision length-based carbon nanotube ladder," published in RSC Adv. 2018, 8, 36049-36055 (2018).
Borzooeian et al., Preparation and investigation on properties of lysozyme chemically bonded to single-walled carbon nanotubes, Journal of Experimental Nanoscience, 2010 (5), p. 536-47. (Year: 2010).
Brunelle et al.. One-dimensional SDS-Polyacrylamide Gel Electrophoresis (1D SDS-PAGE), Methods in Enzymology, 2014(541),Chapter 12, p. 151-59. (Year: 2014).

Chen P, Wu X, Lin J, Tan K. High H2 uptake by alkali-doped carbon nanotubes under ambient pressure and moderate temperatures. Science. 1999;285(5424):91-3.
Cheng J, Cheng SH. Influence of carbon nanotube length on toxicity to zebrafish embryos. International journal of nanomedicine. 2012;7:3731-9.
Coleman JN, Dalton A, Curran S, Rubio A, Davey A, Drury A, et al. Phase separation of carbon nanotubes and turbostratic graphite using a functional organic polymer. Advanced materials. 2000;12(3):213-6.
Dillon AC, Gennett T, Jones KM, Alleman JL, Parilla PA, Heben MJ. A simple and complete purification of single-walled carbon nanotube materials. Advanced Materials. 1999;11(16):1354-8.
Ding Z, Chen J, Gao S, Chang J, Zhang J, Kang E. Immobilization of chitosan onto poly-L-lactic acid film surface by plasma graft polymerization to control the morphology of fibroblast and liver cells. Biomaterials. 2004;25(6):1059-67.
Dong A, Caughey B, Caughey WS, Bhat KS, Coe JE. Secondary structure of the pentraxin female protein in water determined by infrared spectroscopy: Effects of calcium and phosphorylcholine. Biochemistry. 1992;31(39):9364-70.
Dong A, Huang P, Caughey WS. Redox-dependent changes in. beta.-extended chain and turn structures of cytochrome c in water solution determined by second derivative amide I infrared spectra. Biochemistry. 1992;31(1):182-9.
Doorn SK, Fields RE, Hu H, Hamon MA, Haddon RC, Selegue JP, et al. High resolution capillary electrophoresis of carbon nanotubes. Journal of the American Chemical Society. 2002;124(12):3169-74.
Doorn SK, Strano MS, O'Connell MJ, Haroz EH, Rialon KL, Hauge RH, et al. Capillary electrophoresis separations of bundled and individual carbon nanotubes. The Journal of Physical Chemistry B. 2003;107(25):6063-9.
Du et al., Growth of Carbon Nanotubes by Pyrolysis of Thiophene, 111 Journal of Physical Chemistry, 2007, p. 14293-98. (Year: G.2007).
Duesberg G, Blau W, Byrne H, Muster J, Burghard M, Roth S. Chromatography of carbon nanotubes. Synthetic Metals. 1999;103(1):2484-5.
Duesberg G, Muster J, Krstic V, Burghard M, Roth S. Chromatographic size separation of single-wall carbon nanotubes. Applied Physics A: Materials Science & Processing. 1998;67(1):117-9.
Franklin AD, Chen Z. Length scaling of carbon nanotube transistors. Nature nanotechnology. 2010;5(12):858-62.
Goux-Capes L, Filoramo A, Cote D, Bourgoin JP, Patillon JN. Coupling carbon nanotubes through DNA linker using a biological recognition complex. physica status solidi (a). 2006 ;203 (6): 1132-6.
He H, Pham-Huy LA, Dramou P, Xiao D, Zuo P, Pham-Huy C. Carbon nanotubes: applications in pharmacy and medicine. BioMed research international. 2013;2013, 1-12.
Heller DA, Mayrhofer RM, Baik S, Grinkova YV, Usrey ML, Strano MS. Concomitant length and diameter separation of single-walled carbon nanotubes. Journal of the American Chemical Society. 2004;126(44):14567-73.
Holzinger M, Hirsch A, Bernier P, Duesberg G, Burghard M. A new purification method for single-wall carbon nanotubes (SWNTs). Applied Physics A. 2000;70(5):599-602.
Huang W, Taylor S, Fu K, Lin Y, Zhang D, Hanks TW, et al. Attaching proteins to carbon nanotubes via diimide-activated amidation. Nano Letters. 2002;2(4):311-4.
Kong J, Franklin NR, Zhou C, Chapline MG, Peng S, Cho K, et al. Nanotube molecular wires as chemical sensors. science. 2000;287(5453):622-5.
Li F, Cheng H, Xing Y, Tan P, Su G. Purification of single-walled carbon nanotubes synthesized by the catalytic decomposition of hydrocarbons. Carbon. 2000;38(14):2041-5.
Liu C, Fan Y, Liu M, Cong H, Cheng H, Dresselhaus MS. Hydrogen storage in single-walled carbon nanotubes at room temperature. Science. 1999;286(5442): 1127-9.
Liu J, Rinzler AG, Dai H, Hafner JH, Bradley RK, Boul PJ, et al. Fullerene pipes. Science. 1998;280(5367):1253-6.

(56) References Cited

OTHER PUBLICATIONS

Niyogi S, Hu H, Hamon M, Bhowmik P, Zhao B, Rozenzhak S, et al. Chromatographic purification of soluble single-walled carbon nanotubes (s-SWNTs). Journal of the American Chemical Society. 2001;123(4):733-4.

Raffaini G, Ganazzoli F. Protein adsorption on biomaterial and nanomaterial surfaces: a molecular modeling approach to study non-covalent interactions. Journal of Applied Biomaterial and Biomechanics. 2010;8(3):135-45.

Sayes CM, Liang F, Hudson JL, Mendez J, Guo W, Beach JM, et al. Functionalization density dependence of single-walled carbon nanotubes cytotoxicity in vitro. Toxicology letters. 2006;161(2):135-42.

Silverstein et al., Spectrometric identification of organic compounds, 546 Journal of Chemical Education, vol. 39, No. 11, Nov. 1962, 546-553.

Singh B, Saini K, Choudhary V, Teotia S, Pande S, Saini P, et al. Effect of length of carbon nanotubes on electromagnetic interference shielding and mechanical properties of their reinforced epoxy composites. Journal of nanoparticle research. 2014;16(1):1-11.

Tohji K, Takahashi H, Shinoda Y, Shimizu N, Jeyadevan B, Matsuoka I, et al. Purification procedure for single-walled nanotubes. The Journal of Physical Chemistry B. 1997;101(11):1974-8.

Usrey et al.. Controlling the Electrophoretic Mobility of Single-Walled Carbon Nanotubes: A comparison of Theory and Experiment, 23, Langmuir, 2007, p. 7768-76. (Year: 2007).

Vetcher AA, Srinivasan S, Vetcher IA, Abramov SM, Kozlov M, Baughman RH, et al. Fractionation of SWNT/nucleic acid complexes by agarose gel electrophoresis. Nanotechnology. 2006;17(16):4263-9.

Wang et al., "Fabrication of Ultralong and Electrically Uniform Single-Walled Carbon Nanotubes on Clean Substrates", Nano Letter, vol. 9, No. 9, 2 pages (2009).

Wang X, Jiang Q, Xu W, Cai W, Inoue Y, Zhu Y. Effect of carbon nanotube length on thermal, electrical and mechanical properties of CNT/bismaleimide composites. Carbon. 2013;53:145-52.

Yamamoto K, Akita S, Nakayama Y. Orientation and purification of carbon nanotubes using ac electrophoresis. Jounal of physics D: Applied physics. 1998;31(8):L34-6.

Yao Z, Postma HWC, Balents L, Dekker C. Carbon nanotube intramolecular junctions. Nature. 1999;402(6759):273-6.

Yudasaka M, Zhang M, Jabs C, Iijima S. Effect of an organic polymer in purification and cutting of single-wall carbon nanotubes. Applied Physics A. 2000;71(4):449-51.

Z. Borzooeian MET, G. Borzooeian, O. Ghasemi, M. Aminlari. Activity and Stability Analysis of Covalent Conjugated Lysozyme-single walled carbon nanotubes: Potential Biomedical and Industrial Applications. RSC Adv., 2017, 7, 48692-48701.

Ziegler KJ, Rauwald U, Gu Z, Liang F, Billups W, Hauge RH, et al. Statistically accurate length measurements of single-walled carbon nanotubes. Journal of nanoscience and nanotechnology. 2007;7(8):pp. 1-5.

Chevallet et al., "Silver staining of proteins in polyacrylamide gels", Nature Protocols, 2006(1), (Year: 2006), p. 1852-1858.

Kharissova et al., "Dispersion of carbon nanotubes in water and non-aqueous solvents", RSC Adv. 2013(3), (Year:2013), p. 24812-24852.

Pantarotto et al., "Synthesis, Structural Characterization, and Immunological Properties of Carbon Nanotubes Functionalized with Peptides", J. Am. Chem. Soc. 2003(125), (Year: 2003), p. 6160-6164.

* cited by examiner

LENGTH-BASED CARBON NANOTUBE LADDERS

RELATED APPLICATION(S)

This non-provisional application is a continuation-in-part of U.S. patent application Ser. No. 16/383,552, filed on Apr. 12, 2019, which in turn claims priority to provisional application No. 62/656,645, filed on Apr. 12, 2018, both titled "Length-based carbon nanotube ladders," the entire contents of which are incorporated herein by reference.

TECHNICAL FIELD

The present disclosure is generally related to systems and quality control tools for dispersing carbon nanotubes, determining lengths of carbon nanotubes, and determining the distribution of lengths of a collection of carbon nanotubes.

BACKGROUND

Carbon nanotubes (CNTs) of different lengths, diameters and structures are produced using a variety of different methods. Such carbon nanotubes can be employed in a variety of applications, ranging from nano-electronics to semiconductors to probes and interconnects, nanosensors, among others. Geometrical parameters of the carbon nanotubes can have a significant impact on their properties, such as reactivity and conductivity. For example, thermal and electrical conductivities of carbon nanotubes are directly related to their lengths.

Today, manufacturers of carbon nanotubes as well as consumers of carbon nanotubes in a variety of industries, such as consumers in molecular electronics, nanomedicine, nano-biotechnology industries, are facing a major challenge in use of carbon nanotubes, namely, lack of length uniformity of carbon nanotubes in mass production. There is, however, no reliable method for precise and rapid measurement of lengths of carbon nanotubes.

SUMMARY

The following summarizes some embodiments.

The disclosure provides a new ladder standard as a quality control tool for length-based determination and separation of a bulk quantity of carbon nanotubes. A standard ladder according to the present teachings allows obtaining a substantially homogeneous collection of carbon nanotubes in which the lengths of the carbon nanotubes are substantially the same.

In one aspect, a method of length-based separation of carbon nanotubes, determining distribution of lengths of a dispersed collection of carbon nanotubes is disclosed, which comprises conjugating a biomolecule to surfaces of at least a portion of the carbon nanotubes, and separating the conjugated carbon nanotubes having different lengths based on their different charge and size-dependent mobilities.

More specifically, biomolecule moieties, and in particular lysozyme, may be used to functionalize carbon nanotubes, where the biomolecule-nanotube complexes can be readily dispersed and separated based on the lengths of the carbon nanotubes using, e.g., electrophoresis methods and silver staining. In some embodiments, the CNT's are dispersed via conjugation of carbon nanotubes (and in particular carboxylated CNT's) with proteins.

In some aspects, the disclosure relates to methods for the dispersion and length-based separation of dispersed carbon nanotubes (CNT's).

In some embodiments, the conjugation of the biomolecule to the carbon nanotubes can be achieved by carboxylating the carbon nanotubes and covalently linking the conjugated carbon nanotubes to the COOH moieties of the carboxylated carbon nanotubes. In some such embodiments, a linking agent is employed for covalently binding the biomolecule to the surfaces of the carbon nanotubes. By way of example, the linking agent can be a carbodiimide reagent, such as N-ethyl-N'-(3-(dimethylamino)propyl)carbodiimide.

In some embodiments, the conjugated carbon nanotubes can be subjected to gel electrophoresis to cause their separation. By way example, in some embodiments, the gel electrophoresis can be a polyacrylamide gel electrophoresis. In some such embodiments, silver staining is employed to enhance the separation of the conjugated carbon nanotubes achieved by gel electrophoresis.

In some embodiments, the biomolecule can be protein. In some such embodiments, the biomolecule can be an enzyme. In some embodiments, the biomolecule can only be a protein.

By way of example, the enzyme can be lysozyme, such as chicken egg white lysozyme. In some such embodiments, the conjugation of the lysozyme to the carbon nanotubes can be achieved using the carbodiimide method.

In some embodiments, the gel electrophoresis of the conjugated carbon nanotubes results in a plurality of separated bands, each of which corresponds to a particular length of the conjugated carbon nanotubes. In some such embodiments, the location of each band can be analyzed to derive a length of the conjugated carbon nanotubes associated with that band.

In a related aspect, a method for determining average length of a sample of carbon nanotubes comprises labelling each of a plurality of carbon nanotubes with a biological moiety, to provide labelled carbon nanotubes; subjecting the labelled carbon nanotubes to gel electrophoresis, to provide a electrophoresis gel comprising the labelled carbon nanotubes; treating the electrophoresis gel comprising the labelled carbon nanotubes with a visualizing agent to provide stained, labelled carbon nanotubes; and measuring at a plurality of locations in the electrophoresis gel the location of the stained, labelled carbon nanotubes; wherein the average length of the stained, labelled carbon nanotubes is a function of their distance travelled in the electrophoresis gel.

In some embodiments, the carbon nanotubes can be any of multi-walled or single-walled carbon nanotubes.

In one aspect, a kit for determining lengths of a sample of carbon nanotubes is disclosed. The kit includes a standard ladder of reference carbon nanotubes, a conjugation system for conjugating the carbon nanotubes with at least one marker, and an electrophoresis system for separating the conjugated carbon nanotubes according to their lengths.

The kit can further include a system for staining the conjugated carbon nanotubes for facilitating their visualization.

The standard ladder can include a column comprising a polymeric support matrix, and a plurality of reference carbon nanotubes conjugated with a marker, where the reference carbon nanotubes are distributed along the polymeric support matrix in accordance with their lengths. In particular, in some embodiments the reference carbon nanotubes are distributed along the column of the polymeric support matrix such that a distance of a carbon nanotube from top of the column is inversely proportional to a length of the carbon nanotube.

The carbon nanotubes can be any of single-walled or multi-walled carbon nanotube types. The carbon nanotubes can be conjugated to a variety of markers that can facilitate their separation as they migrate along the polymeric matrix in an electrophoresis separation procedure. By way of example, the marker can be a protein or a peptide. For example, the marker can be an enzyme. It has been unexpectedly discovered that lysozyme is a particularly effective marker that allows facile separation of the carbon nanotubes having different lengths on a gel electrophoresis column, such as a polyacrylamide gel.

In some embodiments, the reference carbon nanotubes are stained, e.g., silver-stained to facilitate their visualization and detection.

In some embodiments, the conjugation system can include the aforementioned marker and one or more reagents for facilitating the coupling of the mark with the carbon nanotubes. In some embodiments, the reagents can include at least one of the following:

2-(N-Morpholino)ethane sulfonic acid, N-Ethyl-NO-(3-(dimethyl amino)propyl), Carbodiimide hydrochloride, and N-Hydroxysuccinimide.

Further, in some embodiments, the electrophoresis system can include one or more protein gel casting reagents, and one or more buffers. By way of example, the protein gel casting reagents can include acrylamide, bisacrylamine, tris-HCl, ammonium persulfate (APS), sodium dodecyl sulfate (SDS), and N,N,N,N'-tetramethylenediamine (TEMED).

In some embodiments, the one or more buffers include a sample loading buffer and a running buffer. By way of example, the sample loading buffer can include any of Laemmli buffer or Tris-Glycine SDS, and Tricine/SDS. The running buffer can in turn include Tris, glycine and SDS, Tris, MES/MOPs, Tris/Tricine/SDS.

In some embodiments, the kit can further include at least one dye for sample loading the buffers. By way of example, such a dye can be Bromophenol Blue (3,3-5,5-Tetrabromophenolsulfonphthalein) and glycerol.

In some embodiments, the kit can further include a visualization system for facilitating the visualization and/or detection of the carbon nanotubes. By way of example, such a visualization system can include a silver staining system. For example, the silver staining system can include silver nitrate ($AgNO_3$), sodium thiosulfate ($Na_2S_2O_3.5H_2O$), sodium carbonate ($Na_2CO_3$), acetic acid and paraformaldehyde. The visualization system can also include one or more reducing agents, such as β-mercaptoethanol and dithiothreitol (DTT).

In some embodiments, the kit can include an analysis system, which can be implemented in any of hardware, firmware and/or software. The analysis system can be configured to receive an image of a plurality of bands of carbon nanotubes of a sample under study generated by using the electrophoresis system. The analysis system can be further configured to determine the position of each of the bands relative to a reference position, and to compare the determined positions of the bands with the positions of the bands corresponding to the plurality of reference carbon nanotubes in the standard ladder to determine the lengths of the carbon nanotubes in a sample under study.

In some embodiments, a kit for determining lengths of a plurality of carbon nanotubes in a sample is disclosed. The kit includes a plurality of reference carbon nanotubes conjugated with a marker, an electrophoresis system for generating a standard column using the plurality of conjugated reference carbon nanotubes, a conjugation system for conjugating the carbon nanotubes with at least one marker, and another electrophoresis system for separating the conjugated carbon nanotubes according to their lengths.

In some embodiments of the above kit, the reference carbon nanotubes and the sample of the carbon nanotubes under test are single-walled carbon nanotubes. Further, in some embodiments of the above kit, the marker includes a protein. In some embodiments of the above kit, the marker only includes one or more proteins. By way of example, the protein can be an enzyme, such as lysozyme.

In some embodiments, the marker can be a peptide. In some embodiments of the above kit, the support matrix can be formed of polyacrylamide. Further, in some embodiments of the above kit, the reference carbon nanotubes can be silver-stained so as to facilitate their visualization. In some embodiments, the carbon nanotubes can be stained with an inorganic dye. In some embodiments, the carbon nanotubes have lengths of at least 10 nm.

In some embodiments of the above kit, the conjugation system includes the marker and one or more reagents for facilitating coupling of the marker to the carbon nanotubes. In some such embodiments, the one or more reagents can include at least one of the following: 2-(N-Morpholino) ethane sulfonic acid, N-Ethyl-N0-(3-(dimethyl amino)propyl), Carbodiimide hydrochloride, and N-Hydroxysuccinimide.

In some embodiments of the above kit, the electrophoresis system can include one or more protein gel casting reagents, and one or more buffers. In some embodiments, the one or more protein gel casting reagents can include acrylamide, bisacrylamine, tris-HCl, ammonium persulfate (APS), sodium dodecyl sulfate (SDS), and N,N,N,N'-tetramethylenediamine (TEMED).

In some embodiments, the one or more buffers can include a sample loading buffer, and a running buffer. By way of example, the sample loading buffer can include any of Laemmli buffer or Tris-Glycine SDS, and Tricine/SDS. In some embodiments, the running buffer can include Tris, glycine and SDS, or Tris, MES/MOPs, or Tris/Tricine/SDS.

Further, in some embodiments, the kit can include at least one dye for sample loading the one or more buffers. In some embodiments, the dye can include Bromophenol Blue (3,3-5,5-Tetrabromophenolsulfonphthalein) and glycerol.

In some embodiments, the kit can include one or more reducing agents. By way of example, the reducing agents can include any β-mercaptoethanol and dithiothreitol (DTT).

In some embodiments, the kit can include a visualization system. By way of example, the visualization system can include a silver staining system. By way of example, the silver staining system can include silver nitrate (AgNO3), sodium thiosulfate (Na2S2O3.5H2O), sodium carbonate (Na2CO3), acetic acid and paraformaldehyde.

In some embodiments, the kit can include an image analysis system. The image analysis system can be implemented in any of hardware, firmware and/or software. The image analysis system can be configured to receive an image of a plurality of bands of carbon nanotubes of a sample under study generated by using an electrophoresis system of the kit.

The image analysis system is configured to determine position of each of the bands relative to a reference position. The image analysis system can also be configured to determine an intensity of each of the bands using an image of the bands distributed along the electrophoresis gel.

The image analysis system can be configured to compare the determined positions of the bands associated with a sample of carbon nanotubes under study with the positions of the bands associated with the reference carbon nanotubes to determine the lengths of the carbon nanotubes in a sample under study.

In a related aspect, a standard ladder of carbon nanotubes is disclosed, which includes a column comprising a polymeric support matrix, a plurality of reference carbon nanotubes conjugated with a marker, where the reference carbon nanotubes are distributed along the column based on their lengths. The reference carbon nanotubes can be distributed along the column such that a distance of a carbon nanotube from top of the column is inversely proportional to a length of the carbon nanotube.

The carbon nanotubes in the standard ladder can be any of single-walled or multi-walled carbon nanotubes.

The reference carbon nanotubes can be conjugated with a variety of different markers, such as protein and peptides. In one embodiment, the marker is lysozyme enzyme, which has been found to be particularly effective in facilitating the separation of the reference carbon nanotubes along the column.

By way of example, the polymeric matrix along which the reference carbon nanotubes are separated can be polyacrylamide. In some embodiments, the carbon nanotubes can be silver-stained to facilitate their visualization and/or detection.

In some embodiments, the carbon nanotubes have lengths of at least 10 nm.

In a related aspect, a collection of carbon nanotubes is disclosed, which comprises a plurality of carbon nanotubes dispersed in a medium, wherein the carbon nanotubes have substantially homogenous lengths (i.e., a relative difference between the lengths of any two carbon nanotubes in the collection is at most 10%, or preferably at most 5%). In some embodiments, such a homogenous collection of carbon nanotubes can comprise single wall carbon nanotubes (SWCNTs). The carbon nanotubes can be dispersed in a variety of different media. Some examples of such media include, without limitation, any of reagents such as buffers and organic solvents.

Further understanding of the present teachings can be obtained by reference to the detailed description in conjunction with the associated drawings, which are described briefly below.

BRIEF DESCRIPTION OF THE DRAWINGS

The drawings are not necessarily to scale or exhaustive. Instead, emphasis is generally placed upon illustrating the principles of the embodiments described herein. The accompanying drawings, which are incorporated in this specification and constitute a part of it, illustrate several embodiments consistent with the disclosure. Together with the description, the drawings serve to explain the principles of the disclosure.

In the drawings.

DETAILED DESCRIPTION

Figure 1:
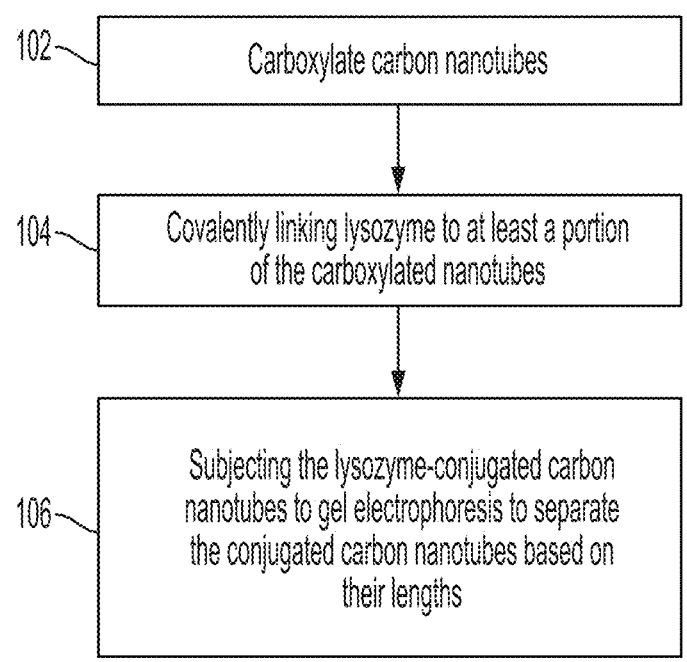
FIG. 1 is a flow chart for length-based separation of carbon nanotubes according to some embodiments.

The following detailed description refers to the accompanying drawings. The same or similar reference numbers may be used in the drawings or in the description to refer to the same or similar parts. Also, similarly named elements may perform similar functions and may be similarly designed, unless specified otherwise. Details are set forth to provide an understanding of the exemplary embodiments. Embodiments, e.g., alternative embodiments, may be practiced without some of these details. In other instances, well known techniques, procedures, and components have not been described in detail to avoid obscuring the described embodiments.

Various terms are used herein in accordance with their ordinary meanings in the art. The term "about" as used herein indicates a variation of at most 5% around a numerical value. The term "substantially" as used herein denotes a deviation of at most 10% relative to a complete state and/or condition.

In one aspect, the present disclosure is generally directed to a quality control tool for length-based separation of carbon nanotubes, measuring distribution of lengths of a collection of carbon nanotubes. In particular, the present teachings provide an indicator for length-based separation of carbon nanotubes (CNTs) via conjugation of one or more biomolecules onto the surfaces of the nanotubes. As discussed in more detail below, in some embodiments, such a method can include conjugating a biomolecule to the carbon nanotubes and subjecting the conjugated carbon nanotubes to silver-stained gel electrophoresis to separate the conjugated carbon nanotubes based on their lengths.

FIG. 1 is a flow chart for length-based separation of carbon nanotubes according to some embodiments.

In step 102, a collection of carbon nanotubes are carboxylated.

In step 104, lysozyme is covalently linked to the carboxylated carbon nanotubes via linkage to their surface COOH moieties. By way of example, carbodiimide method can be used for bio-conjugation of lysozyme onto surfaces of the carboxylated carbon nanotubes.

In step 106, the conjugated carbon nanotubes are subjected to gel electrophoresis to cause separation of the conjugated carbon nanotubes based on their lengths.

Without being limited to any particular theory, lysozyme-conjugated CNTs with different lengths exhibit different mobilities when subject to gel electrophoresis. In particular, covalent attachment of lysozyme to carbon nanotubes can give rise to an intrinsic positive change on any given individual nanotube or bundle of nanotubes, thus affecting their mobilities. In other words, the degree of bioconjugation can affect the separation process and net charge of the carbon nanotubes, thus allowing their separation.

Again without being limited to any particular theory, depending on their length, each conjugated carbon nanotube moves differently through the gel matrix when subjected to electric field. For example, small CNT fragments will experience less resistance when passing through the pores of the gel, while larger ones will experience more resistance. Thus, the conjugated CNTs migrate different distances based on their lengths. In other words, smaller CNTs travel farther down the gel, while larger ones remain closer to the point of loading of the CNTs onto the gel. The velocity (mobility) of the charged CNT fragments is directly proportional to the electric field (E) and the charge of the CNT fragments (q), and inversely proportional to the frictional coefficient of the mass and shape of the fragment (f).

Since the gel acts like a sieve and retains the larger nanotubes while allowing the smaller ones pass through, the frictional coefficient is a representation of the level of resistance that the carbon nanotubes face as they pass through the pores of the gel. As the length of the carbon nanotube is a key factor in its mobility in the gel matrix, one can show that mobility is a decreasing function of the length. In this manner, a ladder of carbon nanotubes can be obtained based on their lengths.

Figure 2:
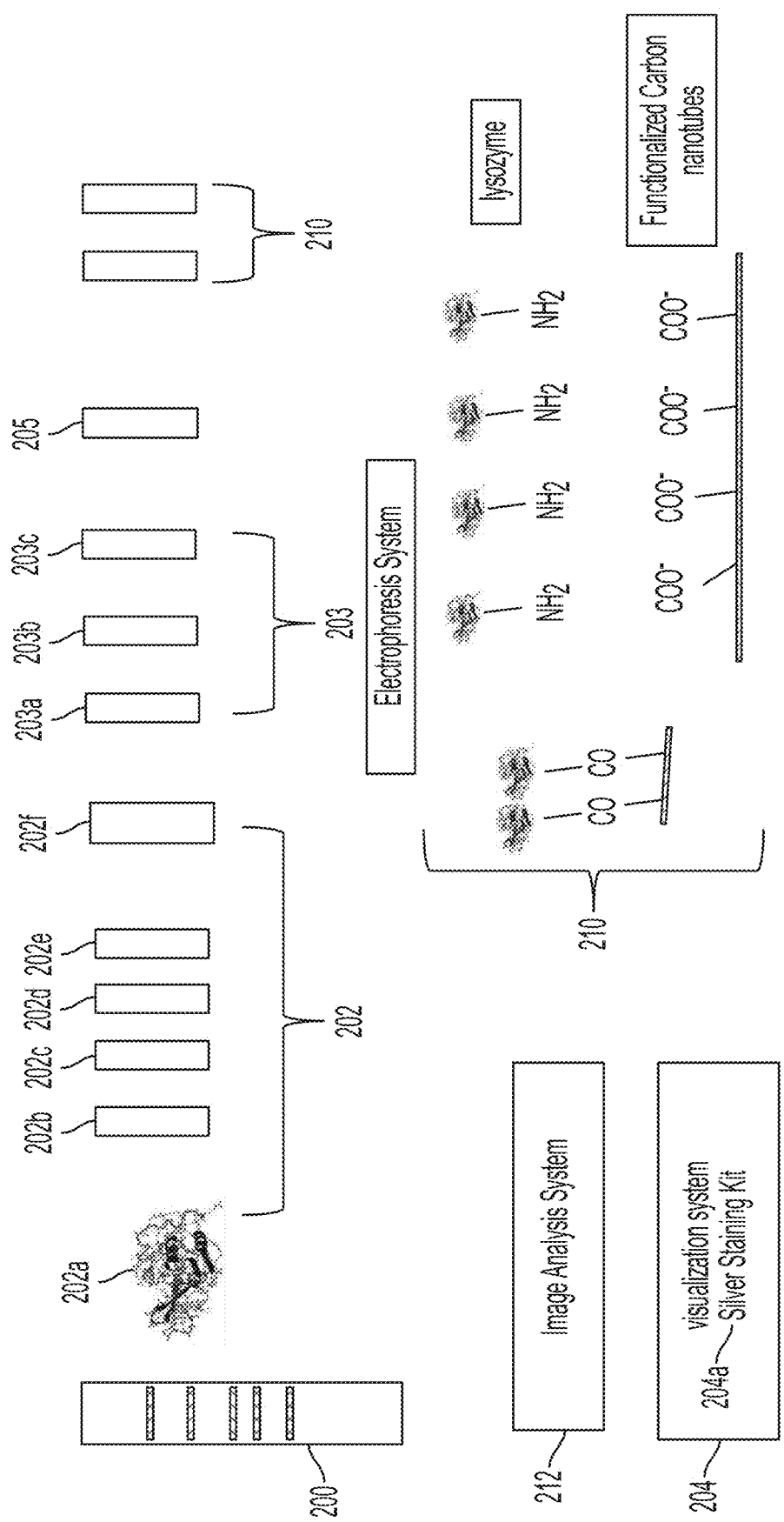
FIG. 2 schematically depicts a kit for use in determining lengths of carbon nanotubes in a sample, according to some embodiments.

FIG. 2 schematically depicts a kit 100 for use in determining lengths of carbon nanotubes in a sample containing a plurality of carbon nanotubes, according to some embodiments. Kit 100 includes a standard ladder of reference carbon nanotubes 200, a conjugation system 202 for conjugating the carbon nanotubes with at least one marker, an electrophoresis system 203 for separating the conjugated carbon nanotubes according to their lengths, a visualization system 204, at least one dye 205, conjugated carbon nanotubes 210, and an image analysis system 212.

Figure 3:
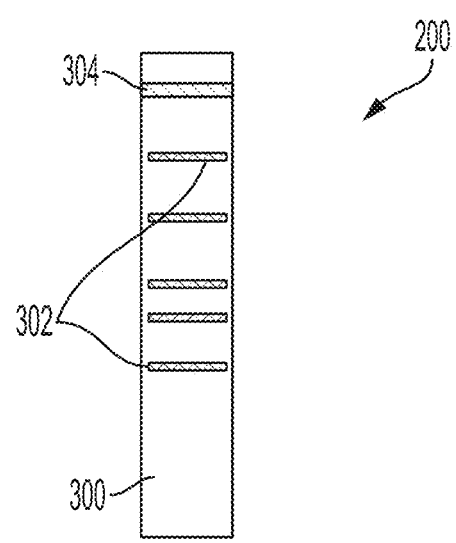
FIG. 3 schematically depicts a ladder according to some embodiments.

FIG. 3 schematically depicts the standard ladder of reference carbon nanotubes 200 according to some embodiments. Ladder 200 includes a column 300, a plurality of reference carbon nanotubes 302, and a reference fiduciary mark 304.

The column 300 is formed of a polymeric support matrix, such as Polyacrylamide or Agarose The plurality of reference carbon nanotubes 302 may be carbon nanotubes with known lengths, conjugated with a marker. The reference carbon nanotubes are distributed along the column in accordance with their lengths. More specifically, the reference carbon nanotubes are distributed along the column such that a distance of a carbon nanotube from the top of the column is a decreasing function of the length of the carbon nanotube. In some embodiments, the reference carbon nanotubes employed to fabricate the standard ladder are single-walled carbon nanotubes. In this manner, the standard ladder of reference carbon nanotubes can be used as a tool to determine the distribution of lengths of carbon nanotubes in a sample under test (SUT), which contains a plurality of carbon nanotubes.

The reference fiduciary mark 304 is located at the top of the ladder from which the distances of the bands of carbon nanotubes corresponding to carbon nanotubes with different lengths can be measured.

Referring again to FIG. 2, in this embodiment the conjugation system 202 includes at least one marker 202a and a plurality of reagents 202b, 202c, 202d, 202e, and 202f.

In some embodiments, the marker 202a can be a biomarker. By way of example, such a biomarker can be a protein (such as an enzyme) or a peptide. For example, it has been discovered that conjugating carbon nanotubes (e.g., carboxylated carbon nanotubes) to lysozyme (the biomarker 202a shown in FIG. 2) is particularly effective in allowing the separation of the conjugated carbon nanotubes on a polymeric support matrix, such as polyacrylamide. Some embodiments may use other markers. Some examples of other markers suitable for use in the conjugation system 202 include, without limitation, whole proteins and peptides used in protein markers and ladders.

The plurality of reagents 202b, 202c, 202d, and 202e may facilitate the coupling of the marker to the carbon nanotubes. In some embodiments, at least one of the reagents can be used to functionalize the carbon nanotubes with any of OH and/or COOH moieties so as to facilitate their coupling to the carbon nanotubes.

In the embodiment shown in FIG. 2, the plurality of reagents 202b, 202c, 202d, and 202e include, respectively, 2-(N-Morpholino)ethane sulfonic acid, N-Ethyl-NO-(3-(dimethyl amino)propyl), Carbodiimide hydrochloride, and N-hydroxysuccinimide.

The reagent 202f may represent one or more reagents for functionalizing the carbon nanotubes to facilitate their coupling to the marker. For example, in such embodiments, the conjugation reagents 202f functionalize the carbon nanotubes with OH and/or COOH moieties.

In some embodiments, reagents 202f may be oxidizing solutions of nitric acid or a combination of nitric and sulfuric acid. Such reagents may be used for functionalizing carbon nanotubes with carboxylic, carbonyl or hydroxyl groups, in liquid-phase reactions. Such functionalization is well known in the art.

Figure 4:
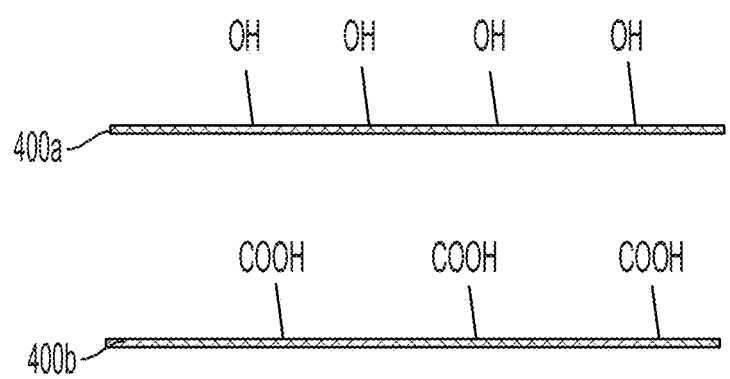
FIG. 4 schematically depicts carbon nanotubes functionalized to include OH or COOH moieties, according to some embodiments.

FIG. 4 schematically depicts two functionalized carbon nanotubes according to some embodiments. In particular, it shows carbon nanotubes 400a and 400b, which are respectively functionalized with OH and/or COOH moieties. The functionalized carbon nanotubes can react with a marker provided in the kit to attach the marker, e.g., via one or more covalent bonds, to the carbon nanotubes.

Referring again to FIG. 2, the electrophoresis system 203 of the kit 100 includes one or more protein gel casting reagents 203a, a sample loading buffer 203b, and a running buffer 203c. In various embodiments, the protein gel casting reagents 203a can include acrylamide, bisacrylamide, tris-HCl, ammonium persulfate (APS), sodium dodecyl sulfate (SDS), or N, N, N, N'-tetramethylenediamine (TEMED). Further, the sample loading buffer 203b can include any of Laemmli buffer or Tris-Glycine SDS, and Tricine/SDS. Further, in some embodiments, the running buffer 203c can include Tris, Glycine and SDS. In some other embodiments, the running buffer 203c can include Tris, MES/MOPS or Tris, Tricine/SDS.

The visualization system 204 includes a silver staining system 204a. The silver staining system can include silver nitrate (AgNO3), sodium thiosulfate (Na2S2O3.5H2O), sodium carbonate (Na2CO3), acetic acid and paraformaldehyde. In another embodiment, the silver staining system can include a silver-ammonia complex. The visualization system can further include one or more reducing agents, which can be used, for example, to reduce the protein disulfide bonds prior to polyacrylamide gel electrophoresis. By way of example, the reducing agent(s) can include any of β-mercaptoethanol and dithiothreitol (DTT).

The at least one dye 205 is used for sample loading the buffers. By way of example, the dye can include Bromophenol Blue (3,3-5,5-Tetrabromophenolsulfonphthalein) and glycerol.

Regarding conjugated carbon nanotubes 210, lysozyme conjugation onto functionalized SWCNTs was achieved using carbodiimide method using N-hydroxysuccinimide (NHS) and N-ethyl-N'-(3-(dimethylamino)propyl) carbodiimide hydrochloride (EDC). The amide linkages form between amine groups of amino acid residues in polypeptides and proteins and carboxyl group of functionalized carbon nanotubes.

The image analysis system 212 is used for determining the lengths of the carbon nanotubes in a sample under study by using the standard ladder as a reference, as discussed in more detail below. The image analysis system can be implemented in hardware, firmware, and/or software.

In one example, in use, a sample of carbon nanotubes under test (SUT) can be functionalized to include OH or COOH moieties. The functionalized carbon nanotubes can then be coupled to the marker using the conjugation reagents discussed above.

The gel casting reagents and the buffers of the kit can be used to form an SDS gel. The one or more loading buffers can then be employed to load the conjugated carbon nanotubes onto one or more wells on the gel. The above one or more running buffers and a voltage applied to the gel can be used to cause the carbon nanotubes to migrate along the gel, and thus separate the carbon nanotubes based on their mass, and hence their length (the mass and length of a carbon nanotube are directly proportional to one another). Without being limited to any particular theory, the gel can act like a sieve, thus providing more resistance to the motion of larger carbon nanotubes relative to smaller ones.

In this manner, a plurality of bands are formed in the gel, where each band corresponds to a particular length of the carbon nanotubes.

The bands formed on the gel can be compared with the bands of the standard carbon ladder to determine the lengths of the carbon nanotubes in the sample. While in some cases, such a comparison can be performed visually, in other embodiments, the comparison can be performed by obtaining an image of the bands associated with the carbon nanotubes of a sample under investigation, extracting information regarding the positions of those bands, and comparing the extracted data regarding positions of the bands with the positions of the bands in the standard ladder so as to extract information regarding the lengths of the carbon nanotubes in the sample.

Figure 5:
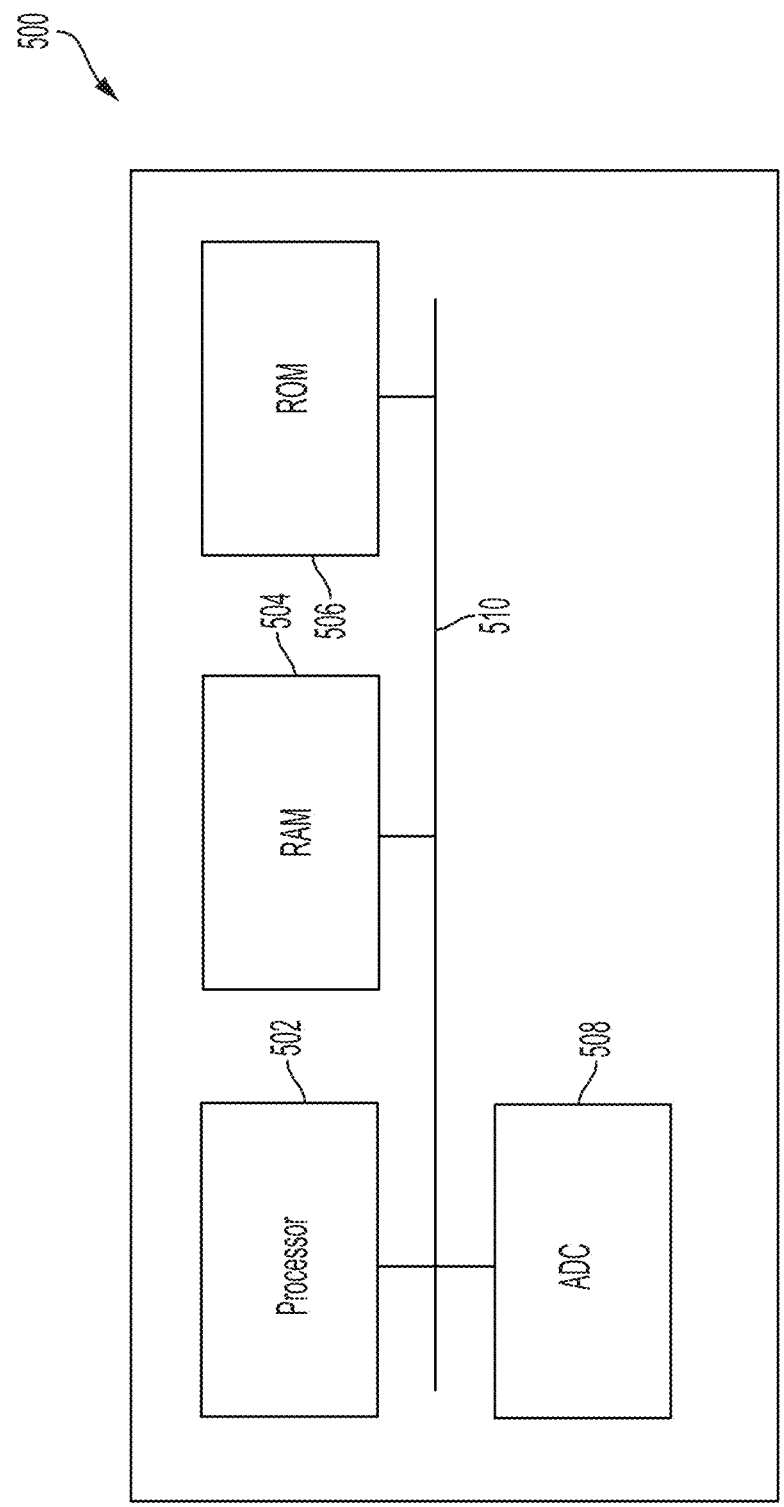
FIG. 5 schematically depicts an analysis system of a kit according to some embodiments.

FIG. 5 schematically depicts an image analysis module 500 according to some embodiments. The image analysis module 500 includes a processor 502, a random access memory (RAM) 504, a permanent memory (ROM) 506, an analog-to-digital converter (ADC) 508 configured for digitizing an image of a carbon nanotube column, and a communication bus 510 that allows the processor to communicate with various components of the analysis module.

In use, the ADC 508 can receive an image of a column of carbon nanotubes under study and digitize and store the image in any of the RAM 504 and ROM 506. Instructions for processing the image according to the present teachings can be stored in ROM 506. During runtime, the processor can effect the transfer of the instructions to the RAM 504 and execute those instructions to process the image and obtain the distribution of the lengths of the carbon nanotubes in the sample under study.

More specifically, a set of image recognition instructions can be stored in the ROM and be executed during runtime to identify a plurality of bands formed on a gel and determine their locations relative to a reference location of the gel. In some embodiments, such a reference location can be provided in each column in proximity of a well into which a sample can be loaded.

In some such embodiments, reference data corresponding to the locations of the bands associated with the standard ladder and the lengths of the carbon nanotubes associated with each band are stored in the ROM 506. During runtime, the extracted locations of the bands associated with the carbon nanotubes in a sample under study can be compared with the reference data to determine the lengths of the carbon nanotubes in the sample. Given that measurement errors are generally present, such comparison of the extracted locations of the carbon nanotubes in a sample with the reference data can provide allowance for such measurement errors. For example, if the location of a measured band falls within about 20%, e.g., at 10%, of an expected reference band, the measured band is assigned to that reference band. In other words, the lengths of the carbon nanotubes of the measured band corresponds to the lengths of the carbon nanotubes in the respective reference band.

In some embodiments, the standard ladder can be generated in the following manner. A sample of carbon nanotubes can be loaded into one or more wells of an SDS gel. Using the distance of each band, in a given lane, from the center (reference point) of the well and the electrical voltage applied to the gel, mobility and consequently the lengths of the CNTs can be calculated using a modified version of Usrey's formula (the formula is discussed in more detail below). An image recognition method, such as that disclosed in the Example section below, can be used for automatic measurement of the intensities and the distances of the bands. The input to the image recognition method can be an inverted image of the gel and the output can be the distance of each band from the center of the well and the average intensity of the pixels associated with each band.

In some embodiments, a kit according to the present teachings, rather than having a pre-made standard carbon ladder, can include the ingredients needed for generating the standard carbon ladder by a user. By way of example, in such embodiment, in the above kit 100, rather than providing the pre-made standard ladder, a plurality of reference carbon nanotubes 210 conjugated with a marker (i.e., conjugated carbon nanotubes with known lengths) can be provided.

A user can generate the standard ladder by forming an SDS gel matrix using the required ingredients provided in the kit and running the reference carbon nanotubes on the gel.

As discussed in more detail below, in some embodiments, such reference ladder can be used to provide quality control of a batch of carbon nanotubes to determine, e.g., the distribution of the lengths of the carbon nanotubes in that batch.

In some embodiments, the reference carbon nanotubes of the standard ladder are single-walled carbon nanotubes (SWCNT). In other embodiments, the reference carbon nanotubes can be multi-walled carbon nanotubes (MWCNT).

In some embodiments, the polymeric matrix is formed of polyacrylamide, though other suitable polymeric matrices can also be employed. In other embodiments, the polymeric matrix can include agarose polymer, which is a linear polymer made up of repeating units of agarobiose, which is a disaccharide made up of D-galactose and 3,6-anhydro-L-galactopyranose.

In some embodiments, the marker to which the carbon nanotubes are conjugated can be a protein. By way of example, in some embodiments, the protein can be an enzyme. By way of example, it has been discovered that conjugating the reference carbon nanotubes to lysozyme is particularly effective in allowing the separation of the carbon nanotubes along the polymeric gel column. In some embodiments, the marker can be a peptide. Some examples of suitable peptides to which the reference carbon nanotubes can be conjugated include, without limitation, whole proteins and peptides used in protein markers or ladders.

In some embodiments, the reference carbon nanotubes can be stained with a suitable visualization aid. By way of example, the reference carbon nanotubes can be stained with an inorganic dye. For example, in some embodiments, the carbon nanotubes can be silver-stained to facilitate their visualization. By way of example, in some embodiments, silver nitrate can be used for silver staining of the carbon nanotubes. In other embodiments, a silver-ammonia complex can be used for silver staining of the carbon nanotubes.

In some embodiments, the lengths of the carbon nanotubes can be, for example, in a range of about 10 nm to about 2 cm, or in a range of about 20 nm to about 1 cm, or in a range of about 30 nm to about 1 micron, or in a range of about 50 nm to about 10 microns, or in a range of about 20 microns to about 100 microns, or in a range of about 200 microns to about 500 microns.

EXAMPLE

The remainder of this disclosure illustrates the methods, systems, and materials according to an embodiment.

I. Conjugation of Lysozyme onto SWCNTs

Conjugation was achieved using carbodiimide method. One mg of CNTs was dispersed in one ml of MES buffer, 50 mM, pH 6.2, and was added to an equal volume of 400 mM NHS in MES buffer. For coupling of NHS to the carboxylic groups on the surface of nanotubes, 20 mM EDC was added to the mixture. The mixture was then stirred at 200 rpm (30 min) followed by sonication for 30 min and then centrifuged at 7000 rpm, three times, 15 min each to remove excess EDC and NHS. The enzyme solution which contained 10 mg of lysozyme in 1 ml of phosphate buffer (10 mM, pH 8) was then added to the nanotubes solution. The final mixture was sonicated for ca. 1 min to re-disperse the SWCNTs. The solution was shaken in an orbital shaker at 200 rpm at room temperature during the conjugation process. The conjugated lysozyme-SWCNTs solution was then centrifuged. To remove all nonspecifically adsorbed enzyme completely, the mixture was washed three times with triply distilled water and once with 1% (v/v) Tween-20. Control enzyme-nanotube conjugates were prepared using the same procedure, only without using EDC and NHS.

II. Characterization of Conjugated Lysozyme-SWCNTs

The morphology of conjugated SWCNTs with lysozyme was compared with that of activated SWCNTs and pure lysozyme using scanning electron microscopy, TGA, X-ray diffraction at $\lambda=0.1542$ nm, and FTIR spectroscopy. To prepare three different ladders of SWCNTs, conjugated samples were sonicated for three time periods of 3, 7 and 10 minutes.

III. SDS-PAGE and Silver Staining

To prepare the gel stock solution (30%, m/v), acrylamide (29.2 g) and Bis (0.8 g) were dissolved in 100 ml of water and filtered. The separating gel solution was made up of 10.0 ml of the gel stock solution, 10.0 ml of Tris-HCl (1.5 mol L-1, pH 8.80), 200-800 µl of $(NH4)2S2O8$ (10% m/v) and 0.4 g of SDS, diluted with water to 40 mL. The stacking gel was prepared by mixing 1.33 ml of the gel stock solution with 2.5 ml Tris-HCl (0.5 mol L-1, pH 6.80) and 50 µL, $(NH4)2S2O8$ (10%, m/v), and diluting with water to 10.0 mL. Then TEMED (10 µL) was added to the mixture. To remove any noncovalently-adsorbed enzyme, samples were washed several times with phosphate buffer (10 mM, pH 8). Electrophoresis buffer was made by dissolving Tris (15.14 g), glycine (72.05 g), and SDS (5 g) in 500 ml of distilled water. Solution's pH was adjusted to 8.30. The final gel which consisted of separating (10.0% m/v) and stacking (3.0%, m/v) gels was made in a vertical polyacrylamide gel system. Sample volumes of 15 µL were loaded on the gel. The silver staining procedure (Blum method 23) consisted of several steps: fixation with methanol, acetic acid and paraformaldehyde solutions, washing with ethanol (50% and 30%) and ddH2O, sensitizing with $Na2S2O3.5H2O$, washing with ddH2O, impregnating with silver nitrate and paraformaldehyde solution, washing with ddH2O, developing with Na2CO3, paraformaldehyde and $Na2S2O3.5H2O$ solution, washing with ddH2O, and ending reaction with a stop solution-methanol 50%, and acetic acid 12%.

IV. Image Analysis Techniques for Length Measurement

Two methods, a manual approach using ImageJ, a NIH approved software, and semi-automated method MATLAB® used to analyse the gel images. Using the distance of each band, in a given lane, from the center (reference point) of the well and the electrical voltage applied to the gel, mobility and consequently length of the CNTs were calculated using Usrey's formula. A MATLAB® code was developed to measure the intensities and the distances automatically. The input to this code was the 8 bit inverted image and the output was the distance of each band from the center of the well and the average intensity of the pixels of each band.

V. Results and Discussion

Carbodiimide method 19, 21, 25 was used for bio-conjugation of lysozyme onto carboxylated carbon nanotubes surface. The results from SEM micrographs (FIGS. 6A-6D; before and after conjugation), TGA results (FIG. 2) used for evaluation of chemical functionalization of SWCNTs and XRD patterns (FIG. 3) and FTIR (FIG. 4) for evaluation of bio-conjugation and its chemical stability, confirmed the attachment of lysozyme onto the SWCNTs surface.

Figure 6A:
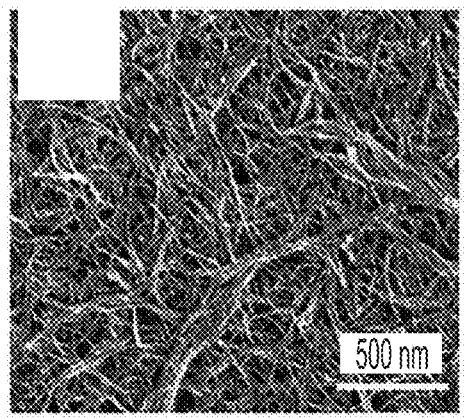
FIGS. 6A-6D show SEM images of SWCNTs before and after conjugation according to an embodiment.
Figure 6B:
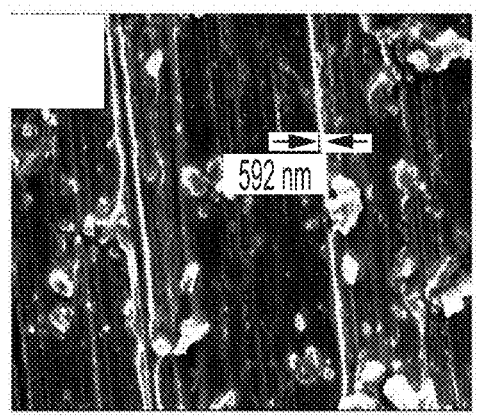
Figure 6C:
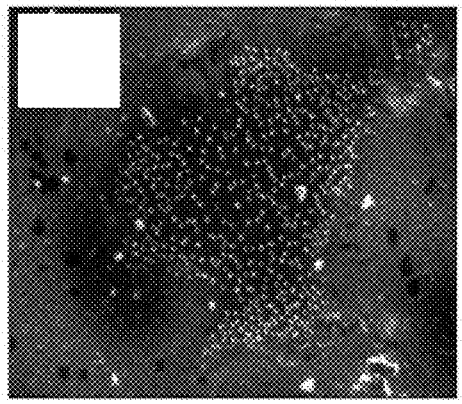
Figure 6D:
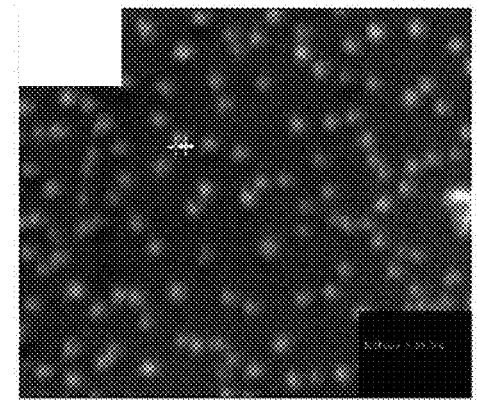

FIGS. 6A-6D show SEM images of SWCNTs before and after conjugation. In particular, FIG. 6A shows the SWCNTs before conjugation, and FIGS. 6B-6D show SEM images of conjugated lysozyme-SWCNTs, with FIG. 6B at a magnification 1.50K (diameter of the SWCNT bundle 592 nm), FIG. 6C at a magnification of 10 K, and FIG. 6D at a magnification 30.0K (diameter of conjugated lysozyme-SWCNT 89.5 nm).

The SEM micrographs (FIGS. 6A-6D) show the pre and post size and morphology of the conjugated SWCNTs. An increase of about 89.5-95 nm in the wall thickness of the conjugated nanotubes is an indication of a successful conjugation.

Figure 7A:
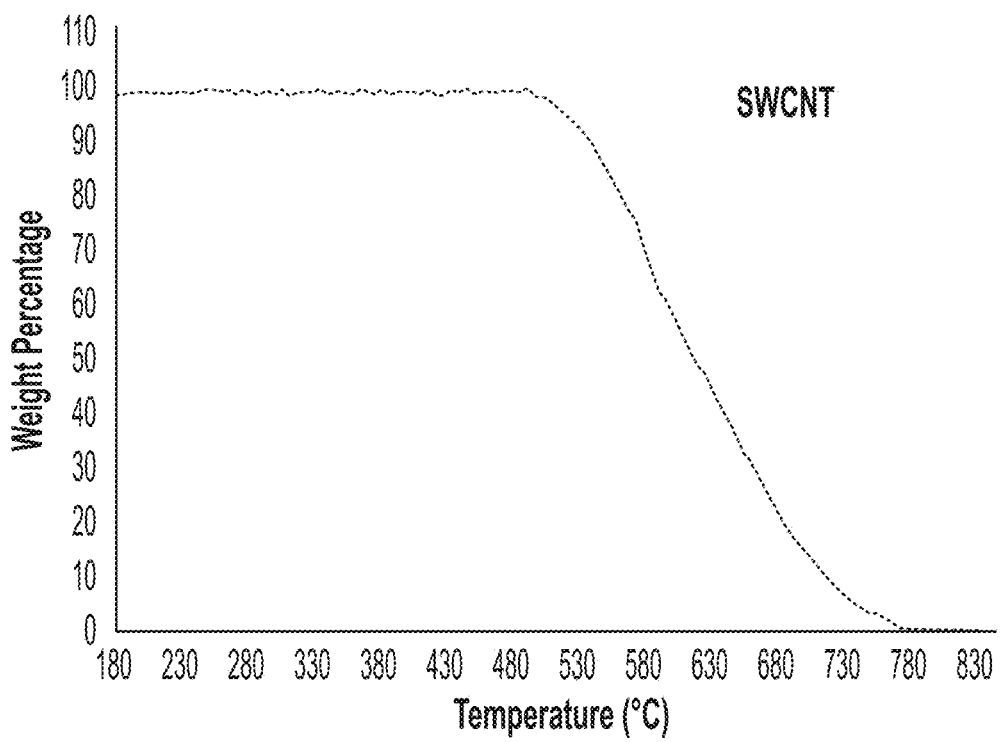
FIGS. 7A and 7B respectively show thermograms of pure and functionalized SWNT with COOH according to an embodiment.
Figure 7B:
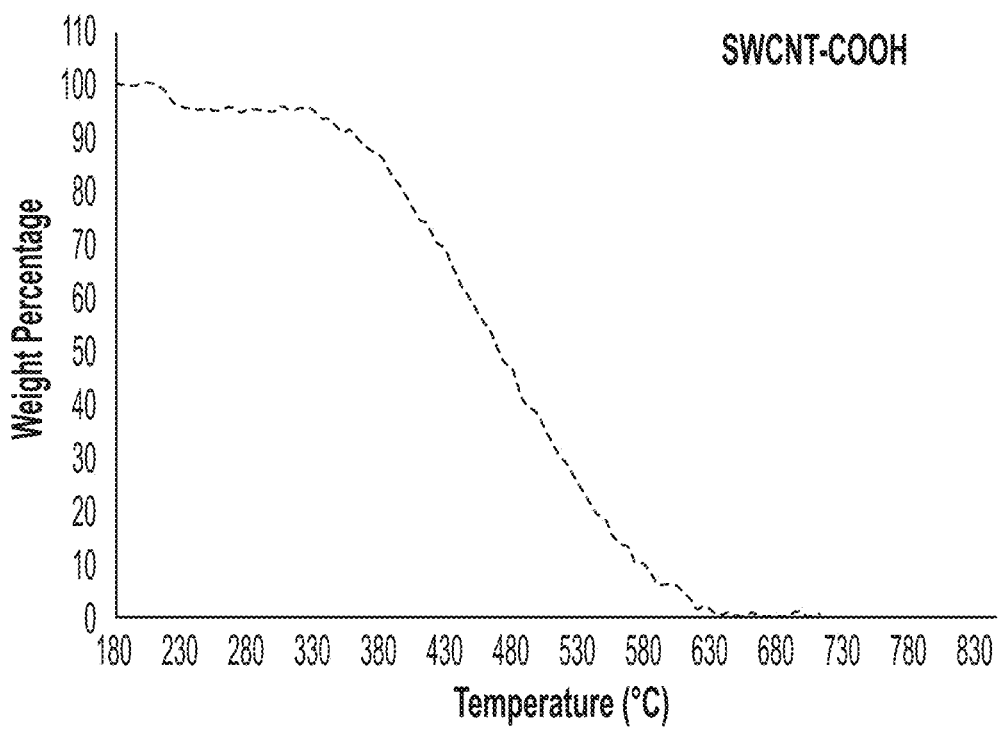

FIGS. 7A and 7B respectively show thermograms of pure and functionalized SWNT with COOH. Loss of weight with temperature is due to the burning of the attached chemical entities to the carbon nanotubes or nanotubes decomposition at elevated temperatures. Weight losses in two temperature ranges of 213-225° C. and 340-600° C. correspond to combustion of the covalently-linked —COOH and burning decomposition of the carbon nanotubes, respectively. As shown in part a), SWCNT is thermally stable up to a temperature of about 500° C. indicating that it has no attached functional groups.

Figure 8:
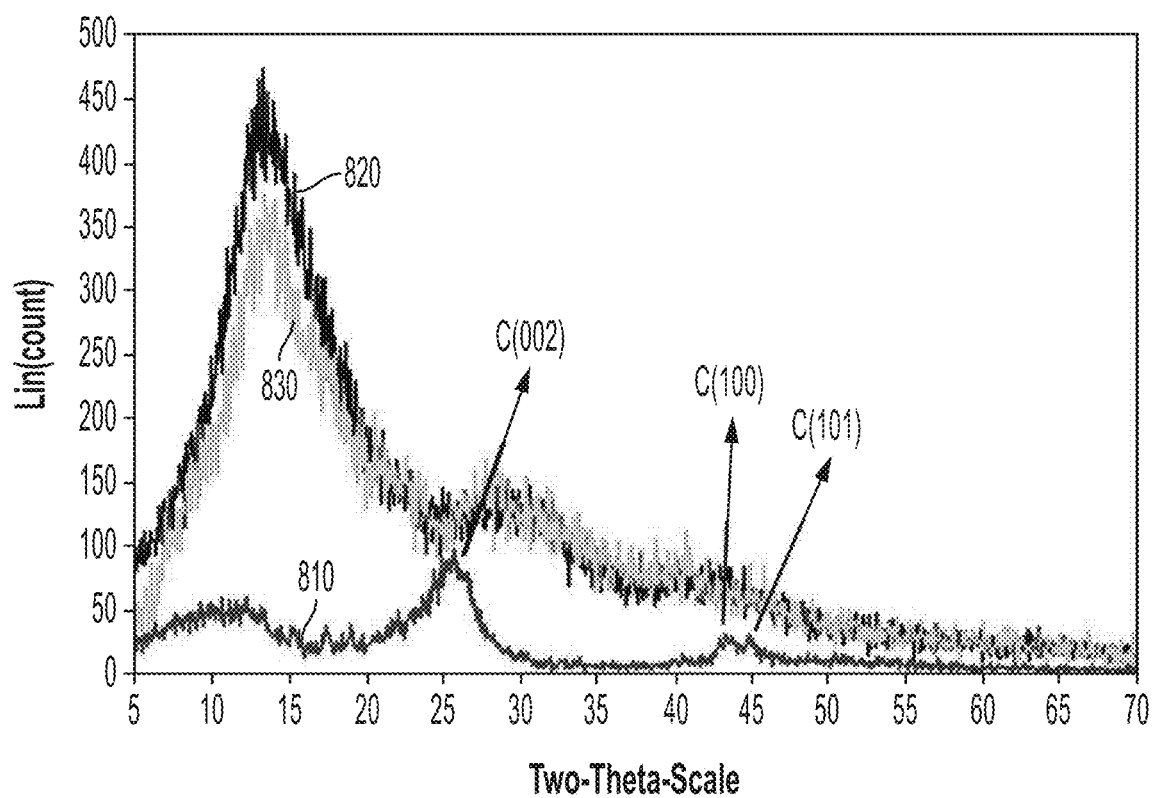
FIG. 8 shows X-ray diffraction (XRD) patterns of SWCNTs (graph 810), lysozyme (graph 820), and Conjugated lysozyme-SWCNTs (graph 830) according to an embodiment.

FIG. 8 shows X-ray diffraction (XRD) patterns of SWCNTs (graph 810), lysozyme (graph 820), and Conjugated lysozyme-SWCNTs (graph 830). SWNCTs peak carbon planes are (002), (100) and (101). The Characteristic peaks of both free and conjugated lysozyme are the same and occur at 2o positions 14.0, 30.0 and 42.0. The identical XRD patterns confirm the adsorption or absorption of lysozyme onto SWCNTs with no lysozyme phase change.

Figure 9:
FIG. 9 shows a table listing the results of XPS analyses according to an embodiment.

FIG. 9 shows a table 900 listing the results of XPS analysis of the atomic concentrations of oxygen and nitrogen in SWCNT, SWCNT-COOH, and Lysozyme-SWCNT. The higher oxygen content for the SWCNT-COOH, compared with the pristine carbon nanotubes, confirms the presence of carboxyl groups on the surface of the nanotubes. The significant increase in both surface oxygen and nitrogen contents in conjugated lysozyme-SWCNTs indicates the covalent bonding between carboxyl-functionalized SWCNTs and lysozyme. The amount of immobilized enzyme was 1.1 mg/mg measured by elemental analysis of the activated carbon nanotubes and the lysozyme-SWNTs conjugates.

VI. FTIR Analyses

The amide linkages between the amino acid residues in polypeptides and proteins are detected in the FTIR diagrams. The covalent immobilization of polypeptides/proteins are studied by detecting the amide types I and II bands in the FTIR spectra, which indicate the conformational changes in the protein secondary structure.

Figure 10:
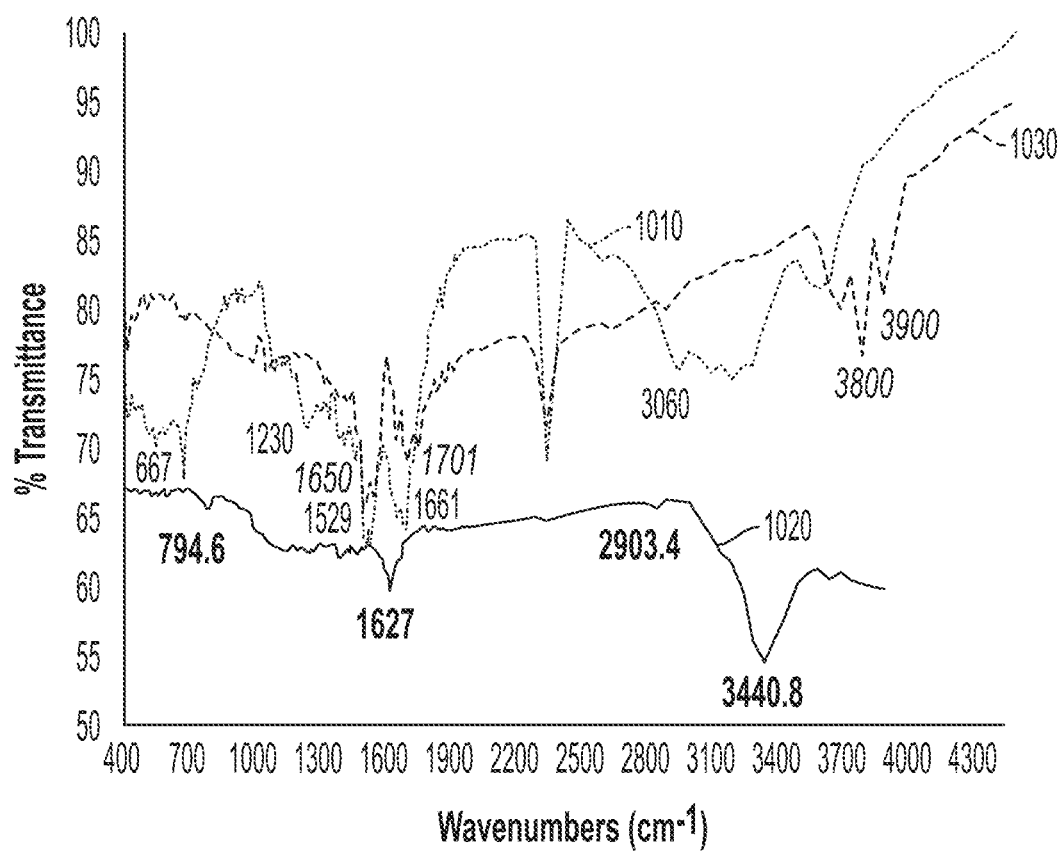
FIG. 10 shows the FTIR spectra according to an embodiment.

FIG. 10 shows the FTIR spectra for pure lysozyme (1010), pure SWCNTs (1020), and lysozyme-SWCNT (1030). Chemical functionalization of SWCNTs with —COOH groups are confirmed by the position of two absorption peaks at 1627.8 cm-1 and 3440.8 cm-1 (black curve). The wide and strong NH stretching band of 2950-2600 $cm^{-1}$ in the enzyme spectrum is the amino acid characteristic. The plateau region near the band of 2222-2000 $cm^{-1}$ corresponds to a combined bending vibration and torsional oscillation of the asymmetrical NH3+28. A weak bending band of asymmetric NH3+ around 1661 $cm^{-1}$ and a rather strong symmetric bending band around 1529 $cm^{-1}$ are also observed. The 3600 $cm^{-1}$ and 1230 $cm^{-1}$ peaks represent the stretching of the N—H and C—N groups in the amine groups, respectively. Looking at the lysozyme-SWCNTs spectrum, the disappearance of the peaks is due to the formation of amide bonds between the carboxyl groups of functionalized SWCNTs and amine groups of the enzyme. Stretching vibration mode of C=O creates the 1650 $cm^{-1}$ peak and stretching of the N—H groups in the amide group creates the 3800 $cm^{-1}$ and 1650 $cm^{-1}$ peaks. In conclusion, the covalent bonding in the conjugation process was confirmed by the FTIR analyses, comparing the amide linkages between the free and conjugated lysozymes (peaks at 3800 $cm^{-1}$ and 1650 $cm^{-1}$).

Figure 11A:
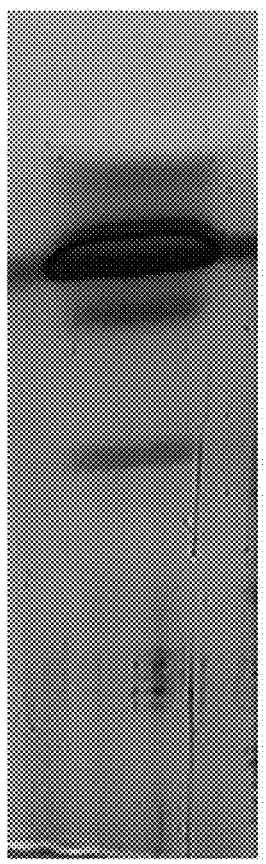
FIGS. 11A-11C respectively show the migration of lysozyme, SWCNTs, and conjugated lysozyme-SWCNTs fragments.
Figure 11B:
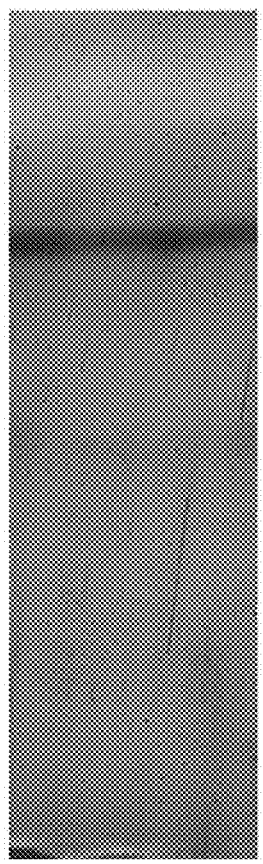
Figure 11C:
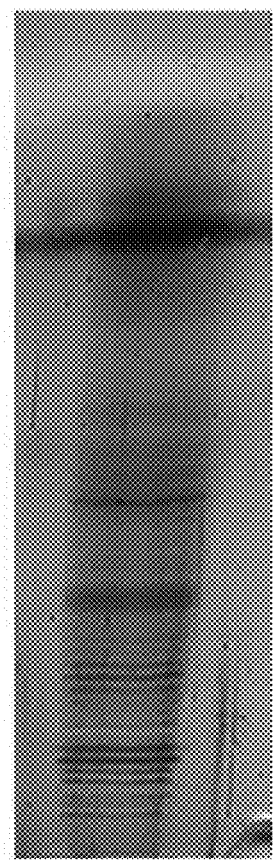

Precise visualization of nanotube fragments in the acrylamide gel which is a challenge for a number of nano-tech researchers, was achieved using silver staining and shown in FIGS. 11A-11C.

The separation process of nano-carbon tubes in the gel based on their length is due to the following effects. Fragments of conjugated lysozyme-SWCNT with different lengths had different mobilities. Covalent attachment of lysozyme to carbon nanotubes gives rise to an intrinsic positive charge on any given individual nanotube or bundle affecting their mobilities. In other words, the degree of bioconjugation plays an important role in the separation process and net charge of fragments is directly proportional to the amount of conjugated lysozyme.

Depending on their length, each conjugated SWCNT moves differently through the gel matrix subjected to electrical field—small CNT fragments will experience less resistance when passing through the pores in the gel, while larger ones have more difficulty. Therefore, the CNTs migrate different distances based on their length. Smaller CNTs travel farther down the gel, while larger ones remain closer to the point of loading. The velocity (mobility) of the charged CNT fragments is directly proportional to the electrical field (E, volts/cm) and CNT fragments charge (q), and inversely proportional to the frictional coefficient of the mass and shape of the fragment (f), as depicted in Eq. (1)

$$V = \frac{Eq}{f} \quad (1)$$

Since the gel acts like a sieve and retains the larger nanotubes while allowing the smaller ones pass through, the frictional coefficient is a representation of the level of resistance that the SWCNT fragments face as they pass through the pores of the gel. The SWCNT fragment length is also a key factor in its mobility in the gel matrix. In view of Eq. (1), one can then show that mobility is a decreasing function of the length, for example, inversely related to length.

To summarize, during gel electrophoresis, the mobility of a SWCNT fragment is primarily a function of its charge/length ratio. Usrey's formula (2), relating the fragment length to the intensity of the bands of the lanes is used for the calculation of the length distribution of the conjugated SWCNTs.

$$L = d \times \exp([3\pi\mu\eta/(q(d) \times e) - 2\ln(2) + 1]) \quad (2)$$

where d=89.0±0.2 (nm) is the average diameter of each CNT and η=viscosity=1.25 (Pa.s), q(d) is calculated according to Usrey et al. and e is the electron charge.

After an analysis of gel images using ImageJ, experimental data were obtained in the form of mobility distribution (number of nanotubes as a function of mobility).

FIGS. 11A-11C show the migration of lysozyme (FIG. 11A), SWCNTs (FIG. 11B) and conjugated lysozyme-SWCNTs (FIG. 11C) fragments across the gel. More specifically, FIGS. 11A-11C show SDS-PAGE electrophoresis and silver staining of lysozyme. (FIG. 11A), SWCNT (FIG. 11B), and Ladder/conjugated lysozyme-SWCNT (FIG. 11C). Stability of conjugation and sensitivity of silver staining technique are the reasons for such sharp bands in FIG. 11C.

Figure 11D:
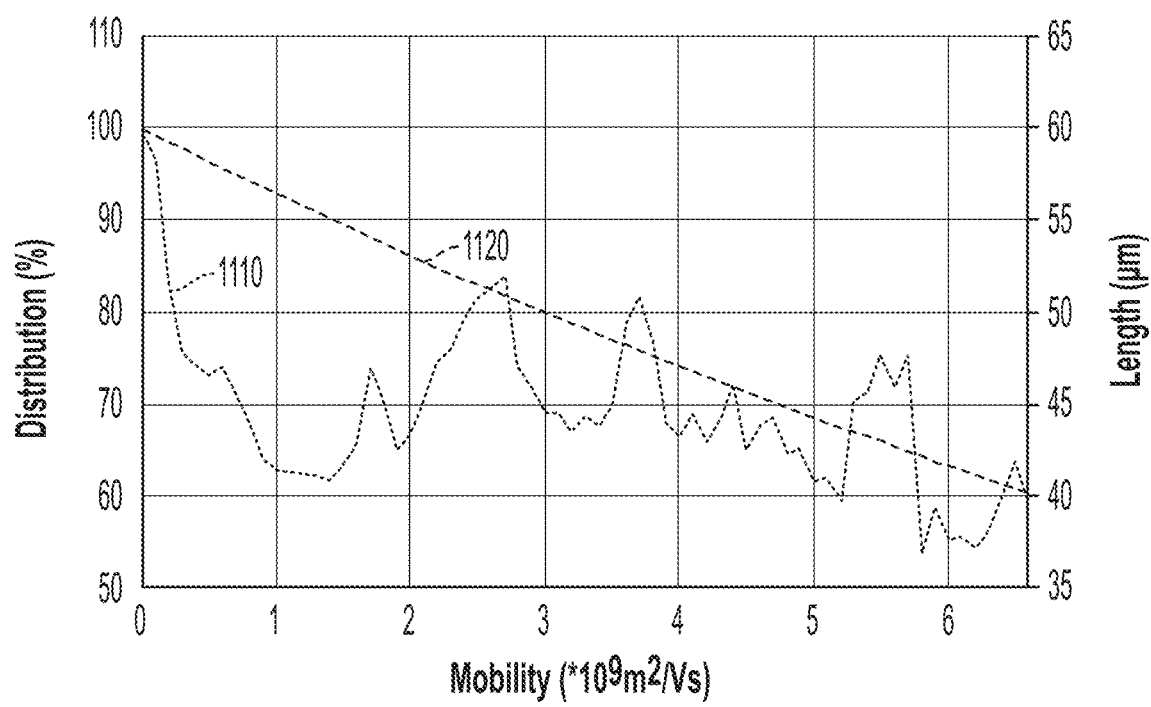
FIG. 11D shows the distribution and the lengths of SWCNT fragments as functions of their mobility according to an embodiment.

Further, in FIG. 11D, graphs 1110 and 1120 respectively show the distribution and the lengths of SWCNT fragments as functions of their mobility. FIG. 11D shows that SWCNTs of various lengths are present in the population for each experimental electrophoretic mobility value.

Figure 12A:
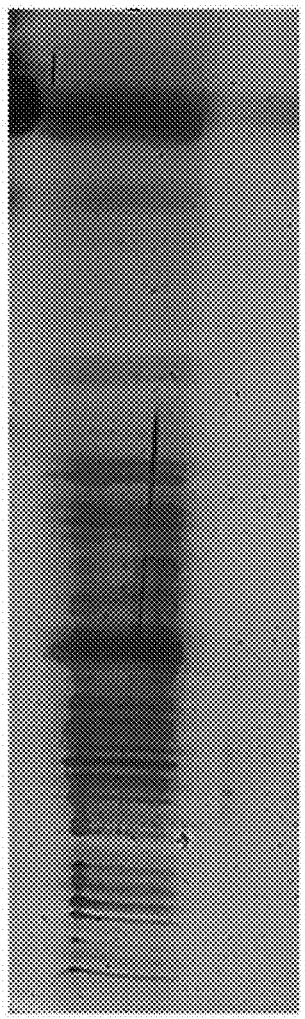
FIGS. 12A-12C show three different ladders of conjugated SWCNT fragments with different lengths according to an embodiment.
Figure 12B:
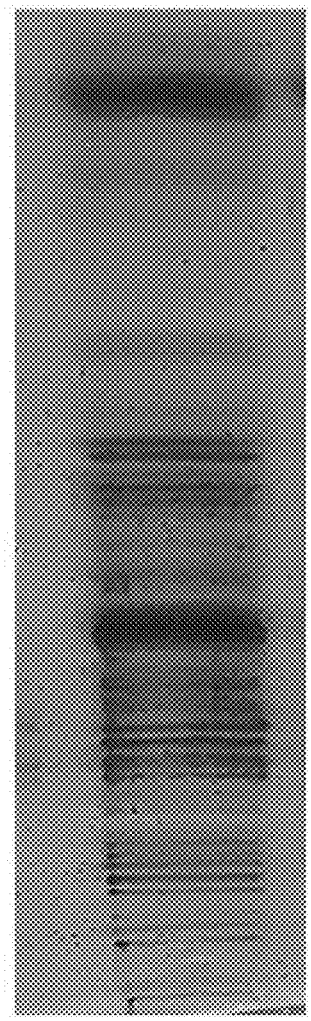
Figure 12C:
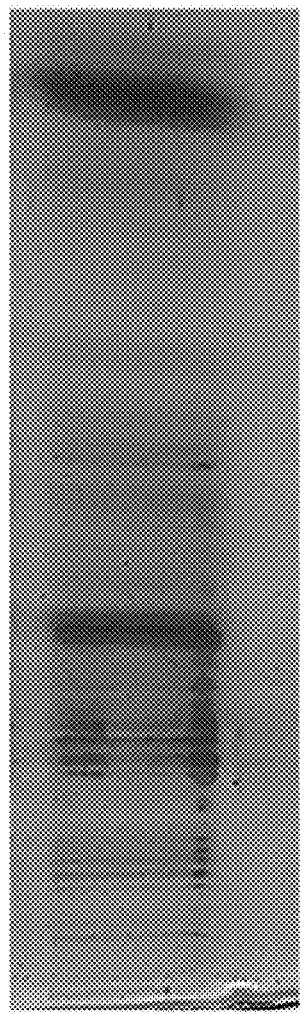

To validate our method of creating CNT ladders, we made three different ladders of conjugated SWCNT fragments with different lengths, produced from sonication intervals of 3, 7, and 10 min (FIGS. 12A, 12B, and 12C, respectively). Conjugated lysozyme-SWCNT fragments of different lengths showed different mobilities.

Figure 13A:
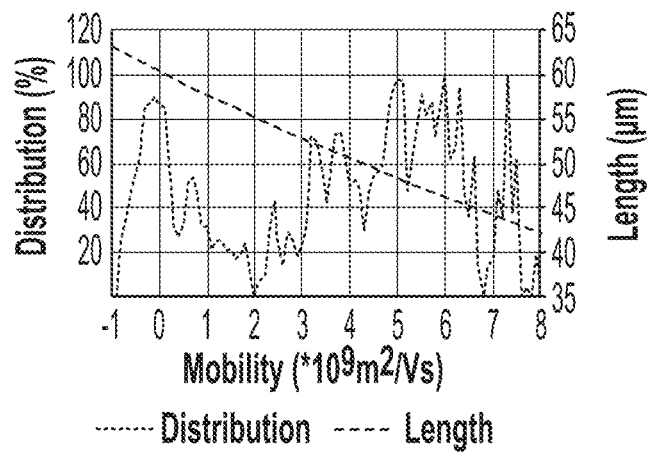
FIGS. 13A-13F show the distribution and the lengths of SWCNT fragments as derived from two methods, according to an embodiment.
Figure 13B:
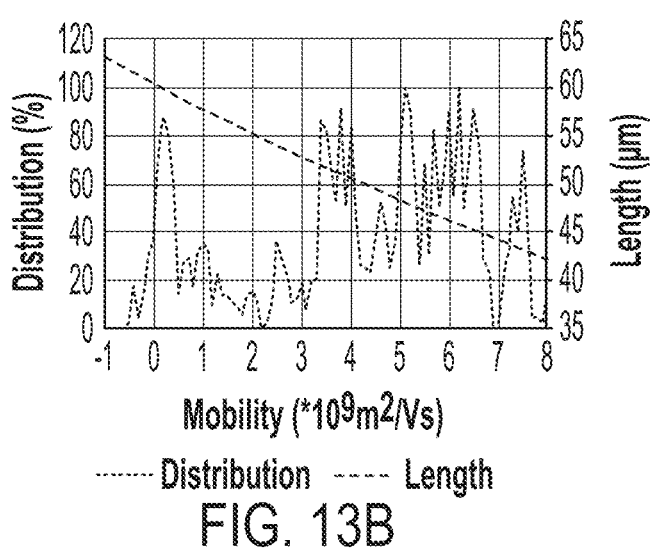
Figure 13C:
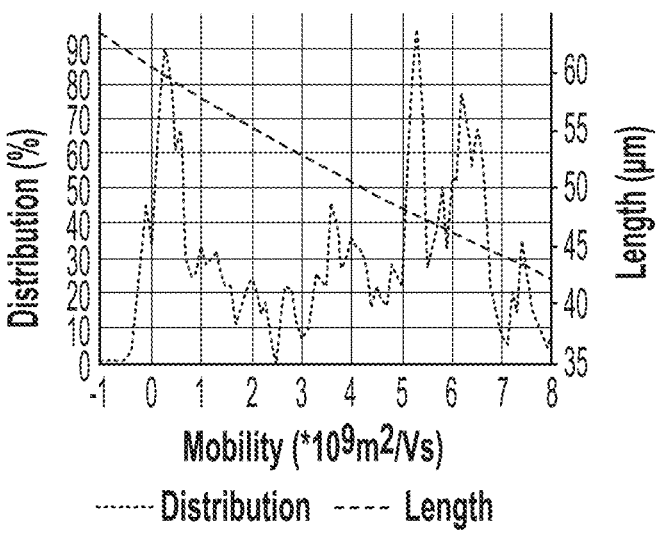
Figure 13D:
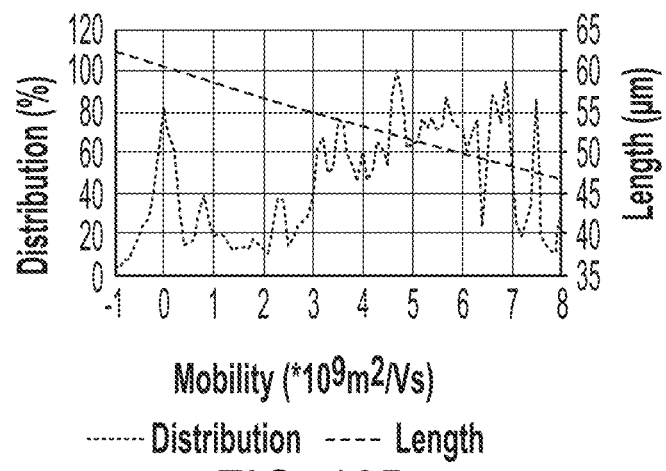
Figure 13E:
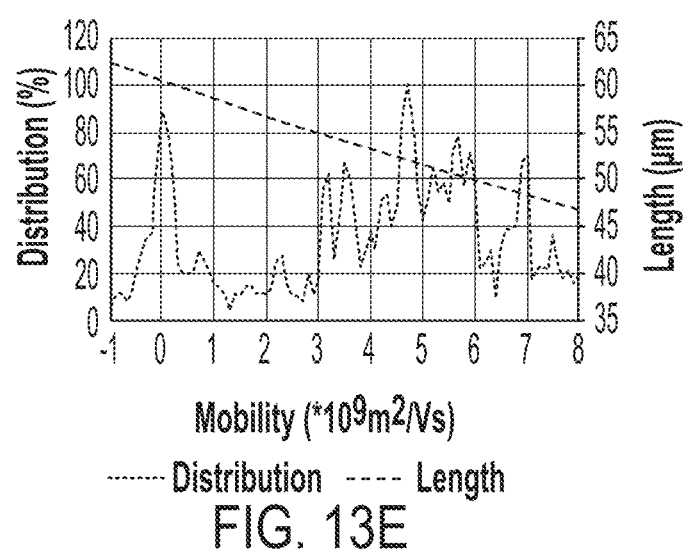
Figure 13F:
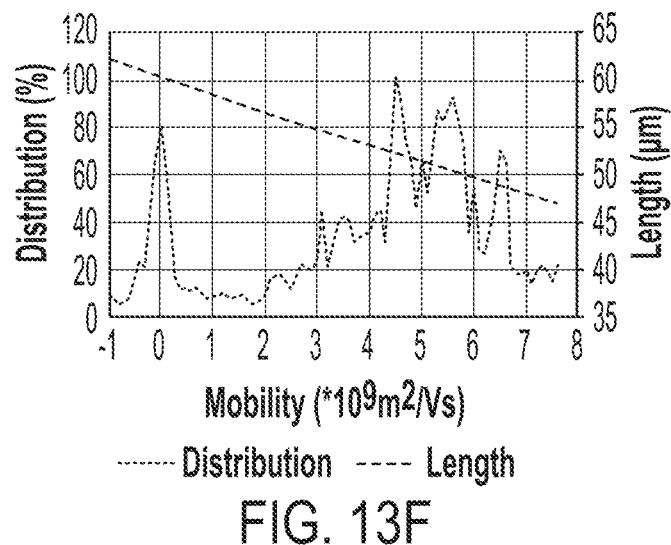

To calculate the length of CNTs, two methods were used. In the first method, a computer program was developed in MATLAB® that subtracts the background, selects three lines on each lane of the gel and averages the signal (intensities of the bands) at each distance from the center of the wells. In the second method, ImageJ is used to calculate the same parameter using a narrow rectangle along each lane from the well to the bottom of the gel. These methods generated similar results (as shown in FIGS. 13A-13F) that are in concordance with the visual evaluations. FIGS. 13A-13F show distribution and the lengths of SWCNT fragments as derived from the two methods, in particular the ImageJ method for FIGS. 13A-13C and the MATLAB method for FIGS. 13D-13F after sonication time at 3 min (FIGS. 13A and 13D), 7 min (FIGS. 13B and 13E), and 10 min (FIGS. 13C and 13F).

After an analysis of gel images, experimental data were obtained in the form of mobility distribution (number of nanotubes as a function of mobility). The corresponding nanotube length of CNTs for every ladder were calculated from the Usrey's formula (2).

Figure 14A:
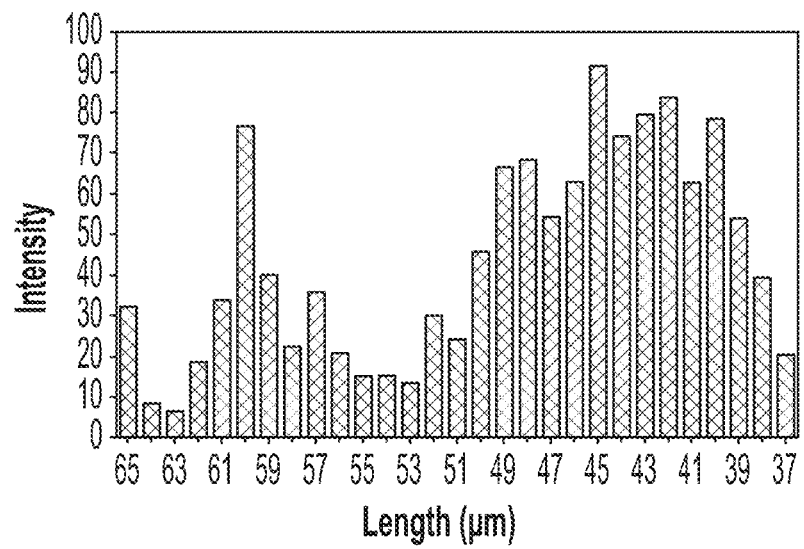
FIGS. 14A-14C show length distributions of the conjugated SWCNTs after sonication for different time intervals according to an embodiment
Figure 14B:
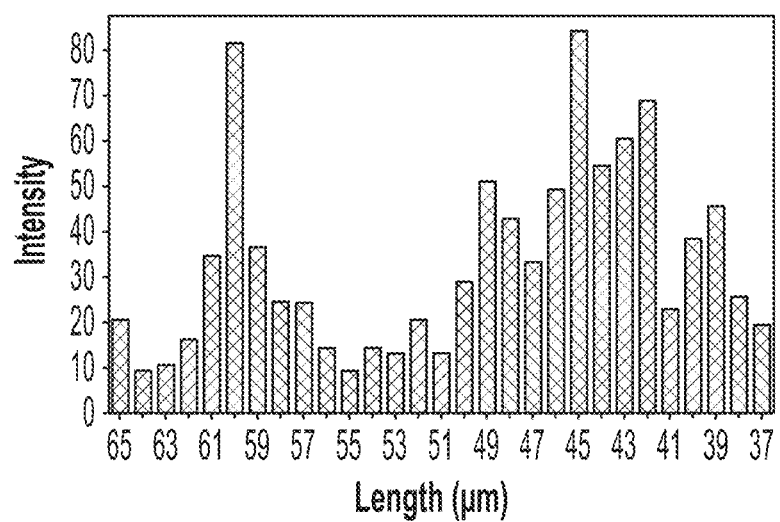
Figure 14C:
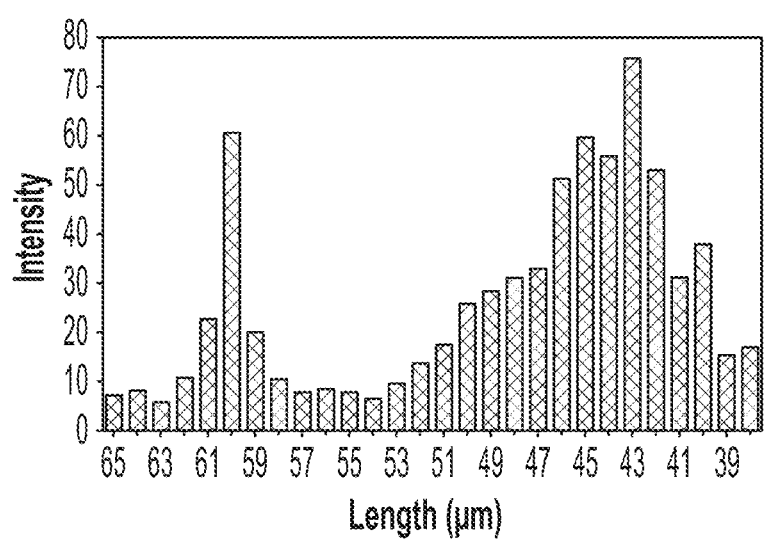

FIGS. 14-14C show length distributions of the conjugated SWCNTs after sonication time at 3 min (FIG. 14A), 7 min (FIG. 14B), and 10 min (FIG. 14C). The intensity of the CNTs at each ladder is plotted versus length of CNTs calculated from equation (2).

While several exemplary embodiments and features are described here, modifications, adaptations, and other implementations may be possible, without departing from the spirit and scope of the embodiments. Accordingly, unless explicitly stated otherwise, the descriptions relate to one or more embodiments and should not be construed to limit the embodiments as a whole. This is true regardless of whether or not the disclosure states that a feature is related to "a," "the," "one," "one or more," "some," or "various" embodiments. Instead, the proper scope of the embodiments is defined by the appended claims. Further, stating that a feature may exist indicates that the feature may exist in one or more embodiments.

In this disclosure, the terms "include," "comprise," "contain," and "have," when used after a set or a system, mean an open inclusion and do not exclude addition of other, non-enumerated, members to the set or to the system. Further, unless stated otherwise or deducted otherwise from the context, the conjunction "or," if used, is not exclusive, but is instead inclusive to mean and/or.

The foregoing description of the embodiments has been presented for purposes of illustration only. It is not exhaustive and does not limit the embodiments to the precise form disclosed. Those skilled in the art will appreciate from the foregoing description that modifications and variations are possible in light of the above teachings or may be acquired from practicing the embodiments. For example, the described steps need not be performed in the same sequence discussed or with the same degree of separation. Likewise various steps may be omitted, repeated, combined, or performed in parallel, as necessary, to achieve the same or similar objectives. Similarly, the systems described need not necessarily include all parts described in the embodiments, and may also include other parts not described in the embodiments. Accordingly, the embodiments are not limited to the above-described details, but instead are defined by the appended claims in light of their full scope of equivalents.

What is claimed is:

1. A gel construct comprising:
   a gel matrix;
   plurality of carbon nanotubes conjugated with a marker and separated into a plurality of bands according to their lengths.

2. The gel construct of claim 1, wherein the plurality of carbon nanotubes comprise a plurality of single walled carbon nanotubes (SWCNTs).

3. The gel construct of claim 1, wherein the marker comprises a protein.

4. The gel construct of claim 1, wherein the marker consists essentially of a protein.

5. The gel construct of claim 3, wherein the protein comprises an enzyme.

6. The gel construct of claim 5, wherein the enzyme comprises lysozyme.

7. The gel construct of claim 1, wherein the marker consists essentially of an enzyme.

8. The gel construct of claim 1, wherein the marker consists of essentially of lysozyme.

9. The gel construct of claim 1, wherein the marker comprises a peptide.

10. The gel construct of claim 1, wherein the marker consists essentially of a peptide.

11. The gel construct of claim 1, wherein the gel comprises polyacrylamide.

12. The gel construct of claim 1, wherein the plurality of carbon nanotubes are silver-stained.

13. The gel construct of claim 1, wherein the plurality of bands includes at least two bands.

14. The gel construct of claim 1, wherein the plurality of bands includes at least three bands.

15. The gel construct of claim 1, wherein the plurality of carbon nanotubes are treated with a visualization agent.

16. The gel construct of claim 1, wherein the gel matrix is silver stained for visualization.

* * * * *